United States Patent
Hans (10) Patent No.: US 12,217,214 B2
(45) Date of Patent: Feb. 4, 2025

(54) MULTI-PATH ELECTRONIC PRESCRIPTION PROCESSING SYSTEM

(71) Applicant: Leo P Hans, Seffner, FL (US)

(72) Inventor: Leo P Hans, Seffner, FL (US)

(*) Notice: Subject to any disclaimer, the term of this patent is extended or adjusted under 35 U.S.C. 154(b) by 0 days.

(21) Appl. No.: 18/531,627

(22) Filed: Dec. 6, 2023

(65) Prior Publication Data

US 2024/0112141 A1 Apr. 4, 2024

Related U.S. Application Data

(63) Continuation of application No. 17/351,603, filed on Jun. 18, 2021, now abandoned, which is a continuation of application No. 14/959,971, filed on Dec. 4, 2015, now abandoned, which is a continuation of application No. 12/337,422, filed on Dec. 17, 2008, now abandoned.

(60) Provisional application No. 61/014,218, filed on Dec. 17, 2007.

(51) Int. Cl.
*G06Q 10/10* (2023.01)
*G06Q 10/107* (2023.01)
*G16H 20/10* (2018.01)
*G16H 40/67* (2018.01)

(52) U.S. Cl.
CPC .......... *G06Q 10/10* (2013.01); *G06Q 10/107* (2013.01); *G16H 20/10* (2018.01); *G16H 40/67* (2018.01)

(58) Field of Classification Search
None
See application file for complete search history.

(56) References Cited

U.S. PATENT DOCUMENTS

| 8,738,393 B2* | 5/2014 | Kobylevsky | G06Q 10/10 |
| | | | 705/2 |
| 2002/0035484 A1* | 3/2002 | Mccormick | G16H 20/10 |
| | | | 705/2 |
| 2004/0006490 A1* | 1/2004 | Gingrich | G16H 40/67 |
| | | | 705/2 |
| 2005/0119912 A1* | 6/2005 | Griswold | G16H 20/10 |
| | | | 705/2 |

FOREIGN PATENT DOCUMENTS

CA 2397925 C * 3/2016 ........... G06F 19/324

OTHER PUBLICATIONS

"A Wireless Cure for Doctors." Wireless Week 5.50 (1999): 36. ProQuest. Web. Sep. 23, 2024. (Year: 1999).*

* cited by examiner

*Primary Examiner* — Lena Najarian
(74) *Attorney, Agent, or Firm* — Christopher Paradies; Paradies Law P.A.

(57) ABSTRACT

An electronic prescription processing system capable of direct two-way electronic communications between a physician practice management system and a pharmacy system uses a multi-path clearinghouse. In one example, the multi-path electronic prescription processing system creates electronic prescriptions with an electronic signature and allows for the interface with the pharmacy computer system such that an image of an electronic prescription and prescription information are directly auto-populated into an entry screen of the pharmacy computer system including specific queries being resolved by the multi-path clearinghouse.

15 Claims, 6 Drawing Sheets

MULTI-PATH ELECTRONIC PRESCRIPTION PROCESSING SYSTEM

REFERENCE TO RELATED APPLICATIONS

This application is a continuation of U.S. patent application Ser. No. 17/351,603 filed Jun. 18, 2021 which is a continuation of U.S. patent application Ser. No. 14/959,971 filed Dec. 4, 2015 which is a continuation of U.S. patent application Ser. No. 12/337,422 filed Dec. 17, 2008 which claims the benefit of Provisional Patent Application No. 61/014,218 filed Dec. 17, 2007, the disclosures of which are hereby incorporated herein by reference.

FIELD OF THE INVENTION

The field relates to electronic prescription systems.

BACKGROUND

Currently, many pharmacists or technicians contact the physician directly through telephone or facsimile, if they have questions with a particular prescription but such a process is time consuming and can be expensive.

U.S. Pat. No. 5,883,370, describes how the physician writes a prescription by entering the prescription into a computer which prints out a bar-coded prescription that may be taken by the patient to the pharmacy, or a future modem path, which would enable the physician to send the prescription directly to a particular pharmacy computer. However, the pharmacist would have to scan the bar code on the prescription and manually enter the prescription into the pharmacy computer or scan the prescription slip bar code into the pharmacy computer directly and the system described is only a one-way system, from the physician to the pharmacist, as disclosed in col. 5, Ins. 16-27. Prior art systems, such as the one described in this reference, do not provide for seamless, automated two-way communications between a prescriber and a pharmacist, however.

U.S. Pat. No. 7,072,840, describes a prescription generation system where patient-identifying data, prescribed drug identification data, drug quantification data, and other prescription information are entered, which are then used to create a prescription. The system does not provide for seamless, automated two-way communications between a prescriber and a pharmacist, and the system has no way of notifying a prescriber if a particular drug in a drug formulary is available at a pharmacy or the price of the drug or the cost of the drug to the patient and/or the patient's insurance company.

SUMMARY OF THE INVENTION

An electronic prescription processing system is capable of two-way electronic communication between a physician and a pharmacy or pharmacist. The system may use a multi-path clearinghouse between the physician's office practice management (OPM) system and a pharmacy computer system. A physician may create electronic prescriptions using an electronic signature. An interface is provided with a pharmacy computer system such that an image of an electronic prescription and prescription information may be directly auto-populated into an entry screen of a pharmacy computer system for. checking and fulfilling prescriptions. In addition, the system processes communications between the pharmacy and the physician's OPM system. A pharmacist may query the physician's office, without any need to speak with the physician or staff by telephone. Preferences may be entered into the processing system for messages internal to the processing system or for notifications by email, text messages, instant messages and the like. The physician's office may respond to individual messages or may batch process a plurality of communications.

In one example, an electronic prescription processing system includes at least one pharmacy system connected to a network capable of two-way digital communications between a plurality of physician office practice management systems and the at least one pharmacy system. The at least one pharmacy system displays an image of the information entered as an electronic prescription by a prescriber using one of the plurality of physician office practice management systems on a display and the information entered as an electronic prescription is auto-populated in entries for a prescription entry screen of the at least one pharmacy system. In one example, a clearinghouse is electronically disposed between physicians' office practice management systems and computer systems for a plurality of pharmacies. One advantage of using a clearinghouse is that each pharmacy system may query, electronically, any of the prescribers, seamlessly and automatically, without speaking by telephone, to resolve questions about the electronic prescription. A multi-path clearinghouse automatically correlates the query with an answer from the prescriber, such as using an unique query identifier, when a prescriber of one of the plurality of physician office practice management systems responds to the query from the at least one pharmacy system.

In one example, a clearinghouse system correlates each of the queries with each of the answers from the prescriber, when the office management systems' responds to the pharmacy using a batch process for answering a plurality of queries from one or more pharmacies. A single electronic transmission from the office management system to the clearinghouse may be used, to communicate with a plurality of pharmacies, for example.

In one example, the clearinghouse provides access to information from a drug file database from one or more pharmacy systems. Then, a prescriber has access to drug inventory and prices, immediately, and can discuss with the patient whether a lower cost alternative that is pharmacologically equivalent or acceptable as an alternative is desired, rather than a more expensive alternative. In another example, a lower cost. pharmacy may be recommended within a reasonable distance from the patient's preferred pharmacy. For example, the clearinghouse is capable of automatically providing notification to the prescriber of alternative prescription items available at the at least one pharmacy and the alternative pricing, and the clearinghouse allows the prescriber the opportunity to substitute an alternative prescription item or alternative pharmacy, electronically, in response-to a query generated by the prescriber's system for entry of an electronic prescription. For example, a clearinghouse system may notify the prescriber, or may provide to the prescriber's system for notifying of the prescriber, generic equivalents available at a pharmacy or an alternative pharmacy, together with pricing information^ such as cost to the patient and/or the patient's insurance company.

In one example, the clearinghouse automatically provides notification to the prescriber of a recalled drug or information that a drug is not recommended for the indications entered into the prescriber's practice management system or electronic health record of die patient. Alternatively, a pharmacy system may provide such information to a physician, either automatically or using an automated, two-way communication protocol between the pharmacist and the prescriber. In addition, a clearinghouse automatically may provide a suggestion of an acceptable alternative to the recalled drug or a drug not suitable for treating a patient with the indications indicated in the patient's electronic health records. The clearinghouse may provide the prescriber an opportunity to substitute the at least one acceptable alternative of a recalled drug, electronically, in response to a query, for example. Alternatively, the query may originate from a pharmacy system upon receipt of a prescription from the pharmacy system.

In one example, an electronic prescription processing system verifies the identity and authority of die prescriber to enter the electronic prescription using an electronic signature, biometric data, a password or a combination thereof. For example, the clearinghouse may be used to authenticate the prescriber using an electronic signature. In another example, a biometric data reader may be used to capture biometric data of a prescriber, and tire electronic prescription processing system, the clearinghouse or the pharmacy system uses the biometric data of the prescriber to authenticate a prescription or a change to a prescription authorized by the prescriber. For example, after a prescription is authenticated by the electronic prescription processing system, the information may be encrypted for transmission to a pharmacy system, such as by a standard public key encryption system, which' may be decrypted by the clearinghouse and/or the pharmacy system using a private key, for example.

In one example, an interface system may be coupled to a physician's office management system, such that the interface system couples the office management system to the clearinghouse and/or the pharmacies' systems, wherein two-way communications are established with the interface system. The interface system is coupled to a data input and editing device and a display, for example. The data input and editing device may include a keyboard, a voice recognition system, a pointing device, a touch screen, a bar code-reader; a scanner or a combination thereof, for example.

In one example, an insurance formulary from an insurance compandor a government insurer is maintained in a clearinghouse, a physician office practice management system, an interface system, or a pharmacy system, and the system is capable of notifying the prescriber, automatically, if a particular prescribed item is not included in the at least one insurance formulary. Then, the system may provide one or more acceptable substitutes for selection by the prescriber, for. example.

In one example, the system includes a database, and all queries and answers to the queries are stored in the database and are tracked, such as within a database of the pharmacy system, for example. An alert may be provided automatically to a prescriber, a pharmacist and/or the clearinghouse, if the prescriber and/or the pharmacist does not timely reply to a query or response in the system, for example. Thus, unnecessary delays may be greatly reduced by managing the timeliness of responses in the system. For example, the system may present an alert to a pharmacist responsible for processing the prescription, automatically, via the pharmacy system, after receipt of an answer from—the prescriber to the query by the pharmacist or the pharmacy system.

A method of processing an electronic prescription uses the electronic prescription system to fill prescriptions after installing pharmacy systems and physician practice management systems and/or interfaces, which are each coupled to a clearinghouse, for example. The system is capable of storing an image of a prescription together with auto-populated fields relating to the image of the prescription in a database and transmits such information from physician office practice management systems to the pharmacies, such as by using the clearinghouse. The pharmacies systems receive the information, which may be stored in a pharmacy database, for processing and filling of a prescription. The information may be displayed on a display of a pharmacist such that the pharmacist is capable of verifying the auto-populated fields of the information in the database against an image of the prescription, for example. A two-way communication protocol for the pharmacist to electronically-query a prescribing prescriber about the prescription and for the prescribing prescriber to provide the pharmacy system with an answer to the query is provided by the system, and querying the prescribing prescriber and receipt of answers to the query is seamless and automatic, providing the pharmacy system with the answer to its specific query, automatically 'notifying' the pharmacist who made the query, or another pharmacist, of the receipt of the answer from the prescribing prescriber.

According to one example, the method may automatically provide for verification and authentication of the prescriber and may be used for verifying that the prescription is ready to be filled. The system may automatically monitor the time elapsed between the time that the query is made and receipt of an answer and may flag delays. For example, a level of urgency may be increased if the answer is not received timely. For example, an elapsed time of two hours without receipt of an answer may prompt notification of the prescriber of a degree of urgency in answering the query. In one example, the alert includes a visual alert on the physician office practice management system. The alert may. include sending an email, contacting a cellphone number or activating a pager, for example. Preferably, the method of alerting should allow the physician to respond seamlessly and automatically, by selecting an answer or by providing comments in a response, and the system will match the response to the respective query, providing an answer to the pharmacist. For example, an email flagged as urgent may provide a selection of yes/no for responding to the query, and wherein selecting yes or no from the selection provides a response to the query, transmitting the response to the pharmacist or another pharmacist.

One advantage of the electronic prescription system is that it allows a physician to use a drug file of an intended pharmacy such that auto-population occurs when the pharmacy receives information from a physician's office. This reduces transcription errors and eliminates transcription costs.

An additional advantage is that once the physician determines which pharmacy the patient uses, the physician may use the actual uploaded drug file information from the selected pharmacy when choosing the patient's medication. Yet another advantage is that the doctor and patient may be informed about the cost of a prescribed medication to the patient and may be provided with lower cost alternatives.

Another advantage is there is no need to have a pharmacy point of sale computer because the electronic prescription system is capable of going directly to and from the physician's practice management system and the pharmacy computer system. All of the normal checks and verifications, such as checking multiple prescriptions for a patient having known adverse interactions may be checked on the pharmacy's computer system. Another advantage is that needless phone calls may be avoided, allowing the pharmacist's question to be resolved, and allowing the prescription to be dispensed.

Another advantage is that failure of a physician to timely response, such as. within two hours, to a query may flag a query as having an increased urgency. Yet another advantage is that the system may alert a physician of an urgent query, such as by an audible, vibrational, visual or other alarm.

Yet another advantage is that the electronic prescription system allows for a two-way communication between the physician and the pharmacist. Yet another advantage is that the need for technician support and the chances of a prescription error are reduced especially errors in communication and transcription of prescriptions.

Still another advantage is the electronic prescription system allows physicians to enter necessary prescription information, reducing errors caused by handwritten prescriptions. Another advantage is a secure system using an electronic signature avoiding prescription fraud. Still another advantage is that an image of the electronic prescription may be directly displayed on the pharmacist computer screen along with the auto-populated information which is found on the prescription entry screen.

An additional advantage is that the auto-population process is integrated into the system and connects directly to the pharmacy computer system, including access to drug files, listing all the drugs which die specific pharmacy uses, including specified generics. Additionally, the drug file may be constantly updated including recall or advisory notices that physician might not otherwise be aware of. Still another advantage is that the system identifies preferred drug switches and sends such information to the physician for a possible switch before the physician even sends out an electronic prescription.

DETAILED DESCRIPTION

The examples described and the drawings rendered are illustrative and are not to be read as limiting the scope of the invention as it is defined by the appended claims. In the drawings, lines of communication are shown by arrows that indicate direction. In each case, the same mode of communication may be used for sending and receiving electronic information or different modes may be used for such as internet, text message, instant message, dial-up access and the like, for sending of receiving electronic information.

The term "physician" is not limited only to a medical doctor, as used herein, but is used broadly to describe any prescriber of medications or other prescription items, such as prescription medical equipment, biologics and the like. The term physician may include a medical doctor, dentist, psychiatrist, surgeon, or the like. The term "physician's office" is intended to include a physician and staff or a physician practice and staff. The term "pharmacy' is intended to include a pharmacist and staff or a pharmacy including at least one pharmacist and staff.

Figure 1:
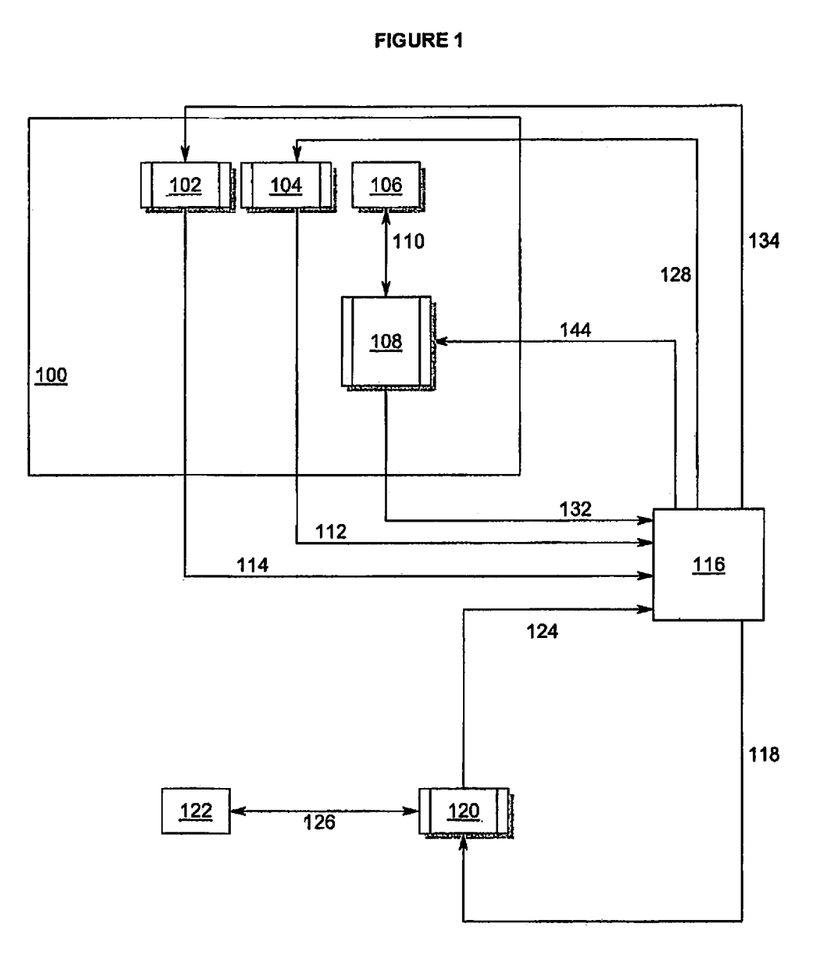
FIG. 1 depicts an example of an electronic prescription processing system process.

In FIG. 1, a plurality of physician's offices may have a computer system which has a type of software used to create prescriptions, billing, patient profiles, etc., which is referred to as an office practice management (OPM) system. An OPM system is connected to the Internet or another system for effective communication with the electronic prescription processing system.

In one example, as illustrated in FIG. 1, a plurality of OPM systems 100 are electronically coupled to a clearinghouse 116, such as by a network such-as the internet, for example OPM system 104 is integrated with an electronic prescription processing system. The OPM system 104 may be a third party system licensed for use by the physician's office. A connection 112 electronically couples the OPM system 104 to a clearinghouse 116. Communication between the clearinghouse 116 and the OPM system 104 occurs via clearing house connection 128, for example. The same connection 112 that is used for coupling the OPM system 104 to the clearing house 116 may be used for two-way communication between the physician's office and the pharmacy, for example.

In one example, a physician purchases or licenses ah OPM system—102—that has an integrated electronic prescription processing system 120 of a pharmacy, for example. Another connection 134, as shown in FIG. 1, couples a clearinghouse 116 to another OPM system 102, and a different connection 114 couples the same OPM system 102 to the clearinghouse 116. The electronic connection 114, 134 may be used for two-way communication between the OPM system 102 and the clearinghouse 116, for example.

In another example, an existing physician practice management system 106, which is not integrated with an electronic prescription processing system, uses an import/export interface with an interface system 108, which may be a stand alone terminal, a virtual machine, or an independent process operating on the same computer system as the OPM system. An interface connection 110 couples the OPM system 106 with the interface system 108, which may include two-way communication between the OPM system 106 and the interface system 108. In one example, a physician's office uses a stand alone terminal 108 to access the electronic prescription system's clearinghouse 116 without the use of any OPM system 106.

An interface system 108 may be coupled to a clearinghouse 116 by interface connections 132, 144, which may use the same channel of communication or different channels, provided that electronic information is passed without human intervention. Digital communication of information and queries are sent electronically avoiding transcription errors, for example. Electronic connection 144 couples the clearinghouse 116 to the interface system 108, using the internet, for example. Alternatively, a single electronic connection may be used for two-way communication. The interface system may be coupled, directly or indirectly, to a data input and editing device and a display, such as a voice recognition system, a keyboard, a pointing device, a touch screen, a bar code reader, a scanner or a combination of these, for example.

A pharmacy connection 124 couples a pharmacy computer system 120 to the clearinghouse 116. Electronic communication between a multi-path clearinghouse 116 and pharmacy computer system 120 occurs via electronic connection 118, for example. In one example, a plurality of pharmacies are coupled to a single clearinghouse 116. In one example, a pharmacy is selected by a patient and/or the physician's office according to availability, price, location or other criteria.

Another pharmacy connection 126 couples a pharmacy computer system 120 to a point of sale system 122 where prescriptions are entered or dispensed. In this example, an internal pharmacy connection 126 is shown as a single two-communication path 126 such as an intranet, an extranet, a wide area network or another private data network. Alternatively, two or more electronic connections may be used, such as the internet or phone lines, power lines, transmitters/receivers, or the like. Information may be secured by encryption during transmissions.

Information, such as patient name, address, insurance information, physician information, and the like, may be entered into any system such as those shown for the OPM systems and/or interface systems 100. Prescription in format may be entered by a point of care physician, for example. In one example, a drug file from a pharmacy 120 is uploaded to the clearinghouse 116 and is sent to the appropriate practice management system that a point of care physician is using, such as an OPM system 102, 104, 106 for example. When a physician's office chooses one or more pharmacies as preferred pharmacies, the physician may have access to the pharmacy drug files, including a list of drugs and generic drugs dispensed by each of the preferred pharmacies, and prices, for example.

Figure 3:
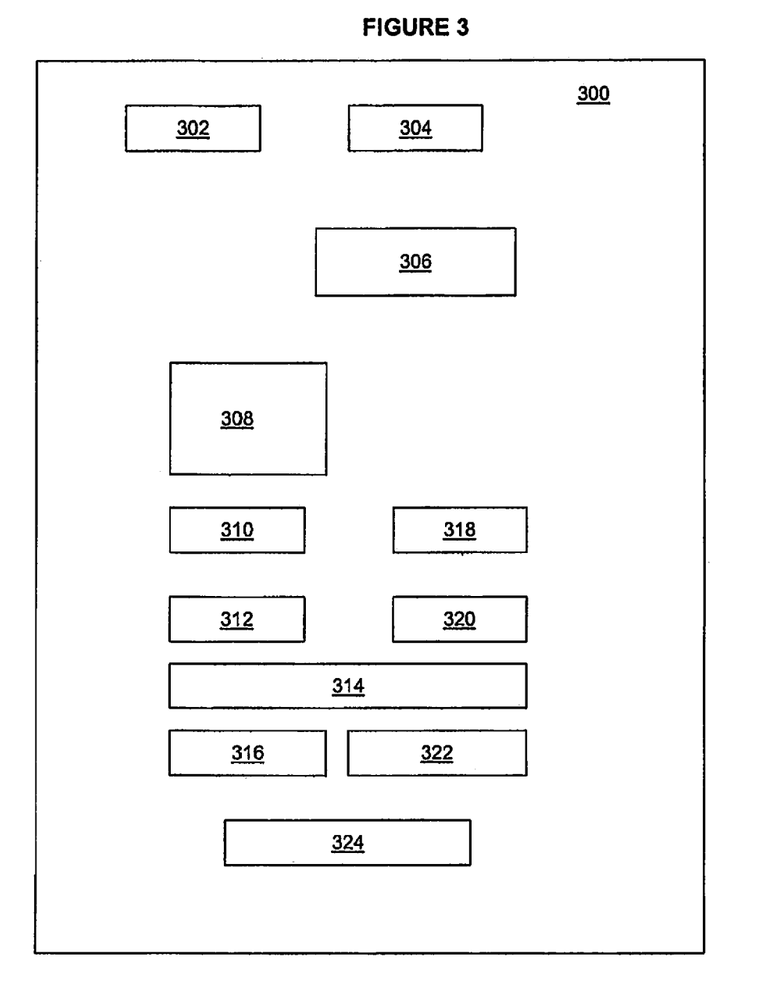
FIG. 3 illustrates an example of an electronic prescription.

Once a particular drug and a pharmacy is selected, then an electronic prescription (e-script) is created. For example, the e-script may include an image 300, a physician electronic signature, biometric data, electronic information identifying the pharmacy, the specific drug or drugs prescribed, patient insurance information, and the like. The physician may review and send the e-script using one of the systems to a clearinghouse 116. For example, the clearinghouse 116 forwards the e-script to the selected pharmacy computer system 120 that is selected by the physician/patient.

The clearinghouse 116 is capable of uploading pharmacy drag files and preferred medications on specific drug plans. The drug files provide the electronic prescription processing system with the ability to notify the physician of suitable alternatives that are included in the patient's drug plan or are available at a reduced cost to the patient, allowing the physician and patient to interchange medications in the same drug category, for example. Once the electronic prescription has been routed to the correct pharmacy computer system, the prescription information may be auto-populated on an existing pharmacy prescription entry screen of the pharmacy computer. The auto-populated screen may contain all the fields used by the pharmacy to process a prescription including an e-script image so that the pharmacist could verify the populated fields against an image of the electronic prescription. Since the physician uses the drug file with the same generics that the pharmacy has or utilizes a brand name drug that could be changed to a generic drug if allowed by the physician, the prescription dispensing would continue as if a pharmacy technician imaged a prescription and entered the appropriate drug file information, without the chance of inadvertent transcription errors, for example. For legal purposes, the electronic prescription with the electronic signature may be printed in the pharmacy and identifying marks (i.e., bar codes) may also be printed for filing. In addition or alternatively, biometric data or an encrypted code, entered by a prescribing physician, may be used to verify the authenticity of the prescription. The electronic prescription system is capable of uploading drug formulary of pharmacies and approved drug formulary of other third parties, such as managed care plans, insurance companies, Medicare and the like. Accordingly, the drug formulary may be patient-specific, depending on which pharmacy and insurance company the patient uses, for example.

Figure 6:
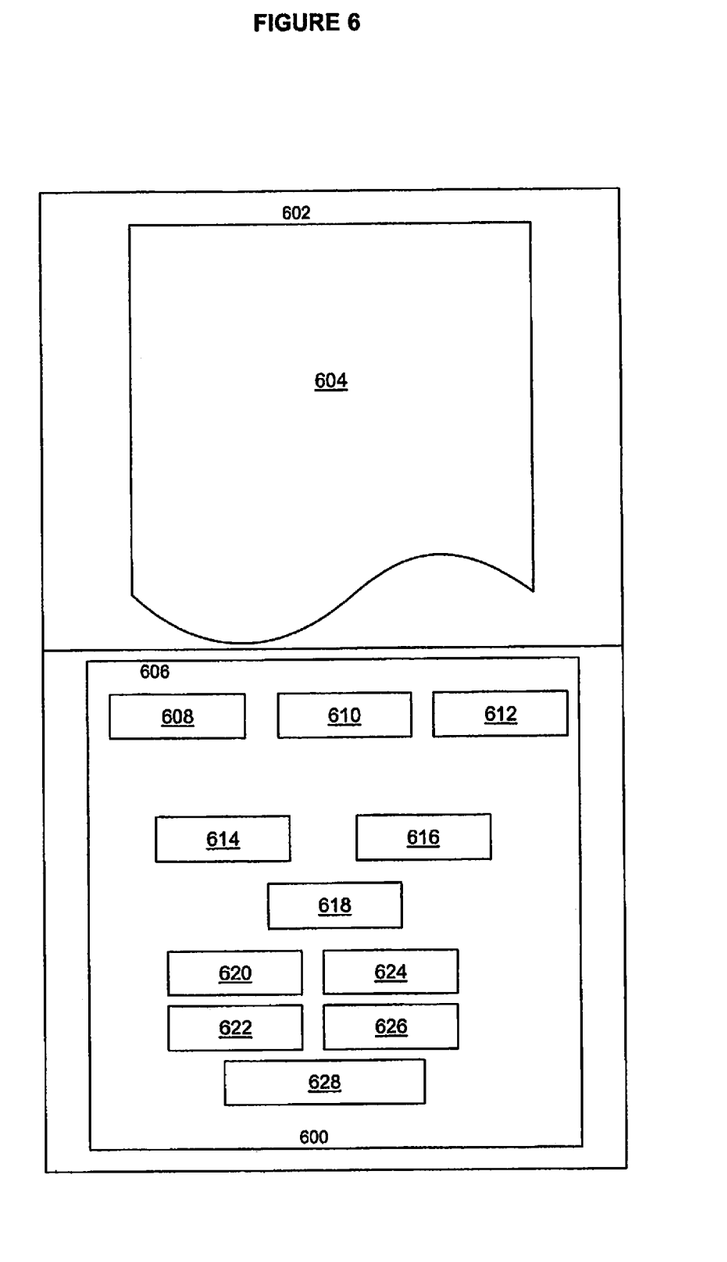
FIG. 6 displays an example of a pharmacist computer screen.

If there are questions about the prescription or how the prescription affects the patient, such as drug interaction, a particular prescription being filled too soon, duplicate therapy, managed care issues and other issues, the physician may need to be contacted by the pharmacist. The pharmacist may use the system to communicate directly with the prescribing physician, such as typing a question in a comment field 628, as shown in FIG. 6. Then, the information and question may be routed using the system to the physician via the clearinghouse 116 or directly. The physician may resolve the issue and send back information to the pharmacy system 120 for review by the pharmacist. The pharmacy may fill the prescription, which is delivered to the patient. In one example, a point of sale system is notified of the status of a prescription on hold for information from the physician. While transcription errors and human error are eliminated, surprisingly, costs are reduced, also, compared to the known system of FIG. 4, for example. Costs that may be reduced include insurance costs, patient costs, costs of filling prescriptions by pharmacies, malpractice insurance costs, and the like. In addition, prescription drug prices, may be reduced by increasing awareness of suitable alternatives and generic equivalents of Mote expensive drugs.

One advantage of the system is HIPAA compliance. The only sharing or exchange of patient identifying information is that required to fill the prescription. Communications between a pharmacist and a physician may be securely encoded, for example. In addition, the pharmacist has the ability to verify patient profile and send in questions to physician's office in order to safely dispense medications without undue delays caused by telephone inquiries. This eliminates the need to call the physician directly, which is a time consuming and costly process that substantially delays filling a prescription, Furthermore, questions may be queued up in a physician's computer, which may be accessed at any time by the physician. Accordingly, the physician's office may answer questions by pharmacists and return answers efficiently as a batch process using the system. In this way, delays in filling prescriptions may be reduced and costs of telephone inquiries eliminated, without interrupting point of care services.

In one example, a communication from a pharmacy computer system 120 is routed through a clearinghouse 116. Unlike known systems, the pharmacy communicates back with the physician using the system. Because of this two way communication feature, communications are improved, costs are reduced and errors reduced. A clearinghouse 116 may upload information about medications, which may be used to notify physician/patient about drugs available at a pharmacy from a pharmacy computer system and/or reimbursed by a specific insurance plans according to an insurance formulary. The system may identify generic equivalents and may provide a mechanism for switching to a preferred drug based on suitable indications, price, availability or a combination of these, for example. The clearinghouse 116 may identify these preferred drugs and may present such information to the physician's office in a standardized electronic form for the physician and/or patient to consider as a better alternative, such as a more suitable alternative for indications or a less costly alternative, for example. Such information may be queued on the physician's office and accessed at the convenience of the physician. If the physician selects an alternative or prefers not to select an alternative, such information may be transmitted to the pharmacy using the system. In one example, this all occurs as the physician is preparing and reviewing the e-script, prior to transmitting the e-script to the pharmacy. In another example, the system automatically provides alternatives after the e-script is received by the clearinghouse but prior to receipt by the pharmacy. The physician may consider if the alternatives are acceptable and may confirm substitution of an alternative prescription, easily. This eliminates phone calls and a wasting of a pharmacist's time, and also has the potential of saving substantial health care costs. Alternatively, messages from and to the physician/pharmacist may be queued up and accessed at a later time. This batch processing improves convenience and has the potential of increasing efficiency. In one example, the pharmacy system may automatically provide suitable alternatives for selection by a physician, based on lower cost, availability, or indications, for example.

Figure 2:
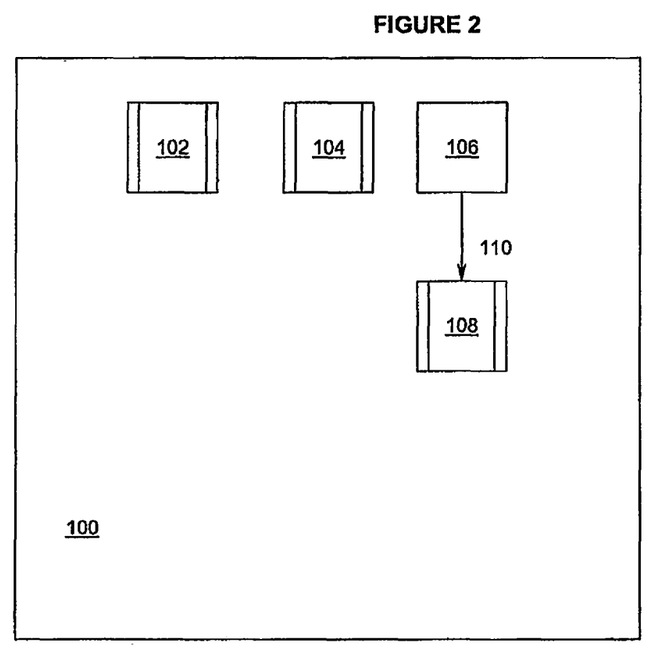
FIG. 2 shows another example.

In FIG. 2, an example of a plurality of OPM systems 100 are illustrated, schematically. An integrated OPM system 102 is an example of a computer system having a practice management system that has an electronic prescription processing system built into it. The integrated practice management system 102 meets multiple office needs (i.e., billing, storing of patient information, appointment schedules, etc.). The vendor of the OPM system incorporates the electronic prescription processing system integrally with these other functions, providing an integrated software package.

Another OPM system 104 is operable with an electronic prescription processing system, seamlessly, but the electronic prescription processing system operates as a separate program either accessing the same database, such as an SQL database, or communicating information to and from the OPM system 104. Such a system 104 would license an electronic prescription processing system utility that is installed together with the OPM system 104.

A pre-existing OPM system 106 may be an older system that is not capable of integrating or communicating with an electronic prescription system directly, for example. Instead, the pre-existing OPM system may, communicate 110 with an interface system 108. The interface system 108 may be capable of extracting data from the pre-existing OPM system 106 and transferring e-script and other communications of the electronic prescription processing system to a pharmacy. Alternatively, the interface system 108 may be used as a stand alone system.

In FIG. 3, one example of an image on electronic prescription 300 is schematically represented. For example, a name field 302 displays the name of the sender, such as a physician. Issue date field 304, for example, is the location the issue date. Doctor information field 306, describes the doctor's name, address, DEA number, and fax number, for example. Patient data field 308 describes foe patient's name, address, date of birth, insurance company, insurance group, and insurance ID number, for example. Drug data field 310 illustrates the drug name and strength. Drug amount field 318 shows the drug quantity to be dispensed. Prescribed usage field 312 provides instructions for the use of the medication. Refill data field 320 indicates refills. Signature field 314 shows an electronic signature by the physician, which is accepted in most states as a valid prescription. In addition, biometric data or a password may be required to authenticate a valid prescription and to reduce counterfeit and fraudulent prescription. Substitution authorization fields 316 and 322, respectively illustrate that the pharmacist may substitute or may not substitute an equivalent for the prescribed medication. Rx ID field 324 depicts the prescription ID mark. In one example, the Rx ID mark/field 324 includes a barcode.

Figure 4:
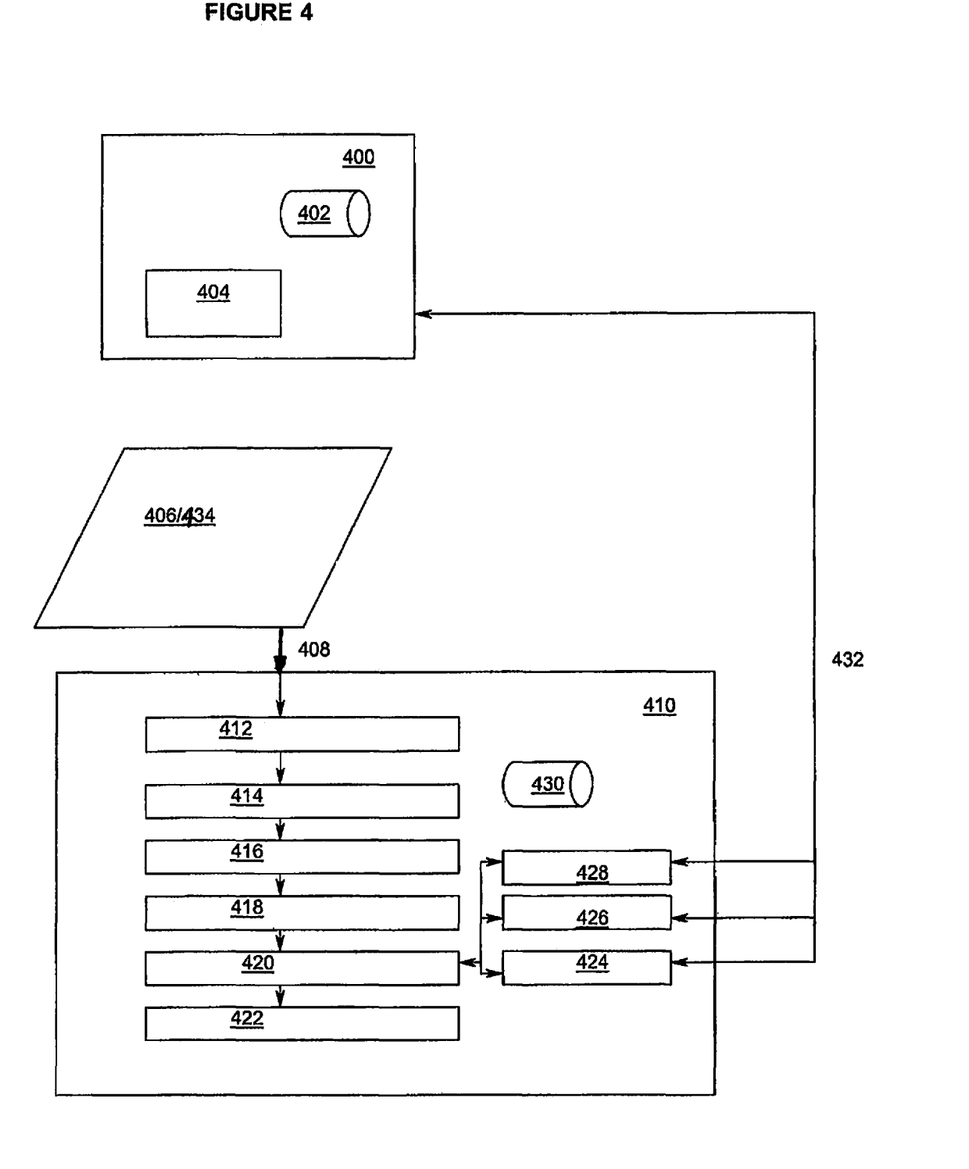
FIG. 4 shows an example of a known prescription process.

In FIG. 4, an example of a conventional process is shown. Doctor's office 400 includes a database 402, and a practice management system 404. Such a system transmits info to the pharmacy via steps 406 or 434. For example, in step 406, the written prescription may be brought in by the patient, or may be mailed, a facsimile may be transmitted of the image of the scrip or otherwise transmitted. In another example, through step 434, information relating to prescriptions maybe communicated to a pharmacy by telephone, telephone network/fax or e-mail without an image of the written scrip. Regardless, either method requires a human to enter the information into the pharmacy system, which is prone to transcription errors, and is time consuming, inefficient, and leaves opportunities for errors to occur.

The data entered from the prescription is transmitted 408 by the pharmacy system 110, which includes a pharmacy database 430. The actual written prescription is received 412 by the pharmacy and is then scanned 414 by the scanning department creating image of the prescription in the computer system. The header entry department enters pertinent information such as physician's name, office information, patient name, insurance information and any other type of information to identify the patient, into the pharmacy computer 416, which may be recorded in the database 430. The drug name, strength, quantity, refills, generic indication, brand indication, and directions are entered 418 by a pharmacy technician.

The pharmacist verifies 420 and then dispenses 422 the prescription; In the verification process 420, the pharmacist may need to call the doctor 428, conduct drug utilization review 426, or contact the managed care department 424, if there is managed care issue. The pharmacy contacts 432 the appropriate office or physician when there are issues about the prescription 428, a drug utilization issue 426, or managed care issue at step 424, for example. In some cases, multiple calls may be necessary to get a complete answer to a question or questions.

When comparing this example with a system using an electronic prescription processing system of the present invention, many differences stand out. By eliminating certain steps a system that provides for direct two-way electronic communication and auto-population of prescription information substantially reduces errors and time required of a pharmacist, the physician and their staff to resolve errors or to request additional information.

Eliminating unnecessary steps, such as scanning 414, data entry 416, 418 and the like reduces costs and errors, for example. Using an auto-populated pharmacy entry screen of the prescription image, such as shown in the example of FIG. 6 allows a pharmacist to quickly verify prescription information, including any alerts, recalls, adverse drug interactions and the like. A pharmacist may pull the information on the screen, scroll down to see additional information about patient information, and verify or check the prescription, without the assistance of a technician that is normally required for data entry and reconciliation, reducing delays and eliminating pharmacy-side labor costs.

Redundant steps, such as contacting 432, multiple offices or physicians about prescription errors 428, drug utilization 426 and/or managed care issues 424, may be eliminated.

For example, automated, two-way physician-pharmacist communication eliminates any need to call 432. The two-way system allows the pharmacist to enter questions in a pharmacist comment field 628, as shown in FIG. 6, for example. Then, the question, alert or notification may be sent to the physician designated to respond in the electronic prescription. Any response from the physician is routed to the e-script, may automatically alert the pharmacist and may be reviewed by the pharmacist, which may be the same pharmacist or another pharmacist working at the same pharmacy who may be designated in the system.

Figure 5:
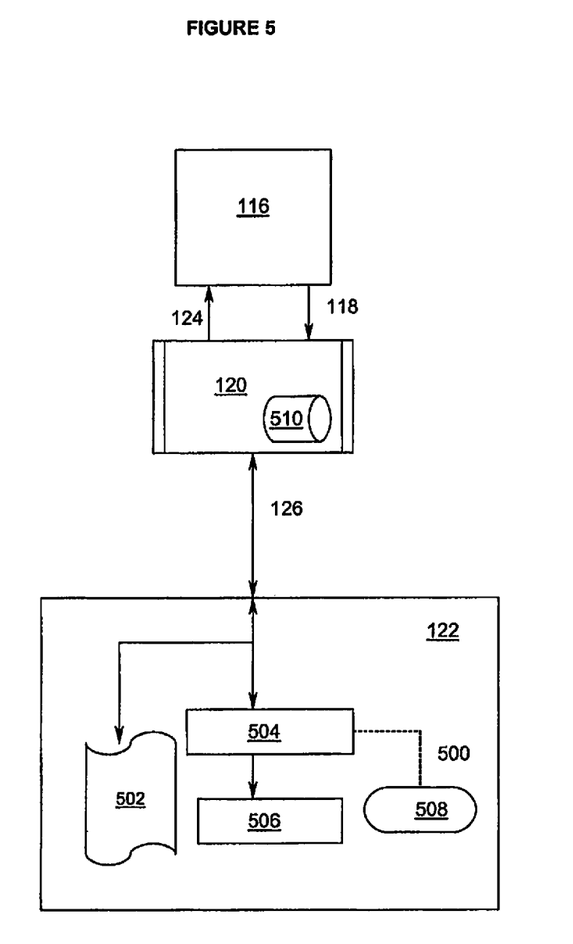
FIG. 5 shows an example of a pharmacy processing a prescription using an example of an electronic prescription processing-system.

In FIG. 5, one example of how a pharmacy processes an electronic prescription is schematically illustrated. Many large pharmacies have a pharmacy computer system that is capable of connecting to all the pharmacy's locations. This may be a network, such as a cloud network, a wide area network or the like. Bach computer at a particular location of the pharmacy communicates with the pharmacy's computer system, which may be a centralized server or mainframe in one example. A clearinghouse 116 sends information to the pharmacy including an e-script. The e-script is delivered 118 to the pharmacy's computer 120 and a pharmacist then verifies the information. A hard copy of an image of the electronic prescription is printed and filed, if desired. One verified a prescription is released 126 to the point of sale location 122 for dispensing to a patient.

In one example, a pharmacy computer system of a chain of pharmacy point of sale locations 122 stores all pharmacy data, electronically, in a centralized database 510. Each chain pharmacy and computer terminal of the chain of pharmacies may be connected to the pharmacy computer system 120 and communications 126 occurs seamlessly. In one example, internal pharmacy communications 126 occur seamlessly with a mainframe, for example. In an alternative' example, a centralized server replaces the mainframe, and all communications are seamless. In yet another example, the pharmacy computer system is a distributed system, and only the database 510 is centralized. A centralized system may inform a distributed system of a newly released prescription ID, and the distributed system accesses information from a centralized database 510. Herein, a centralized database 510 does not infer that all data is stored at a single location. Instead, it means that all distributed systems have access to the same data, which may be stored as a SQL database at one or more storage locations.

Communication 124, 118 between a clearinghouse 116 arid pharmacy computer system 120 may provide for two-way communication, for example. A single electronic connection may be used for two-way communication or multiple modes and pathways may exist to provide two-way communications 118,124.

A pharmacy computer system 120 includes a database 510. Information relating to an electronic prescription is transmitted 126 to the individual pharmacy locations 122. In one example, a local pharmacist verifies the information provided by the electronic prescription 504, an e-script may be printed 502, and the pharmacy dispenses medication associated with a verified e-script to the patient 506. The pharmacist may opt to use a conventional process 508 of filling a prescription by forwarding 500 the prescription for processing according to FIG. 4, for example. Two-way communication 126, electronically, between the pharmacy and the pharmacy system 120 and the clearing house 116 permits safe, secure queries between a pharmacist and the prescribing physician to occur rapidly. Delivery and read status indicators can be used to track progress in resolving discrepancies with one or more offices and/or physicians. Answers may alert the appropriate pharmacist to review the answer and to take further actions as appropriate. All queries and answers may be automatically logged to the pharmacy system database 510 by the pharmacy system 120. Timeliness of responses to queries may be tracked and an additional query may be transmitted, or the urgency of a query may be increased. In on example, a query may be flagged for immediate response or may present an audible, vibrational or other alert, when a response is not timely.

In FIG. 6, an example of a pharmacist computer screen 600 is shown. The pharmacist entry screen 606 includes an image of the prescription on the screen as well as an area to enter information from the image into the pharmacist computer. The system allows information from the physician to be directly presented to the pharmacist. All fields may be auto-populated with information reducing entry and transcription errors. In one example, the pharmacist may edit information on the entry screen 606. The pharmacist may hit a single key or button to release the e-script for filling. Then, a label may be printed, the label may be adhered to a bottle and/or attached to a bag and the corresponding medication may be dispensed. This eliminates many of the steps shown in FIG. 4. Furthermore, communications between pharmacist and physician are greatly enhanced and timeliness is measured and improved.

Prescription image viewer 602 allows visual verification between an image of the prescription 604 and the entry screen 606. In one example, the entry screen 606 includes physician information 608, patient information 610, insurance information 612, drug name 614, drug strength 616, directions 618, quantity 620, days of supply 622, dosages per day 624, refills 626 or any other information necessary for verifying and filling the prescription. The pharmacist comment area 628, may be used by the pharmacist to enter comments or questions for an office or physician. For example, if a prescription needs to be sent back through the system to the prescribing physician for clarification of any questions or alert the physician about any other matter requiring physician interaction, then a pharmacist may enter or select a specific query question, alert or notification and may press a key or button (on screen or otherwise), to transmit the question, alert or notification to designated physician office or other responsible party. For example, the physician or office may receive an alert by text message, email, instant message or the like. An alert may provide notification to the physician to access the physician's OPM system, for example, or may provide a link or access to a reply server, In one example, a clearinghouse 116 sends a message allowing the physician to answer a yes/no question using a cell phone, mouse, pointing device or voice command, for example. Then, a response may be transmitted answering the posed question(s). Biometric data, a password or an electronic signature may be required for authenticating an answer.

In another example, the physician may not have entered a prescription and a pharmacy may enter a prescription subject to approval by the physician. An e-script is maybe transmitted to the doctor for his or her approval with questions or comments. Once the physician answers the questions, which may be required prior to proceeding, the physician may send the electronic prescription to the pharmacy for further processing. In one example, an unique ID and/or password is required to update information stored on a pharmacy computer system, for example.

In one example, the generation system disclosed by U.S. Pat. No. 7,072,840, may be used to generate an e-script, for example. Alternatively, an e-script may be generated by a third party OPM system. A clearinghouse 116 may automatically require population of certain required fields necessary for verification of an e-script by a pharmacist, for example. In one example, the e-script is automatically rejected by the clearinghouse 116 with a request for specific information to be entered into fields of an e-script. An interface program, capable of coupling to a MEPPS system, for example, may auto-populate prescription information for a pharmacist entry screen such as illustrated in FIG. 6. The system may further upload drug formulary of a specific pharmacy or pharmacies and insurance company or companies. For example, a formulary for a managed care plan may alert a physician to availability of alternatives to a drug not included in the formulary or drugs that are less expensive. Thus, alternative prescription items may be suggested or recommended for selection by the physician, Alternative combinations and variations of the examples provided will become apparent based on this disclosure. It is not possible to provide specific examples for all of the many possible combinations and variations of the embodiments described, but such combinations and variations may be claims that eventually issue.

What is claimed is:

1. An electronic prescription processing system for processing of an electronic prescription for at least one pharmacy system coupled to a network, the at least one pharmacy system including a pharmacy system database, the electronic processing system comprising:

a multi-path clearinghouse electronically coupled to the network and coupling over the network the at least one pharmacy system to a plurality of physician office practice management systems, each of the plurality of physician office practice management systems having at least one prescriber, the at least one pharmacy system comprising the pharmacy system database with fields such that the fields are auto-populated with information from the electronic prescription and an image of the electronic prescription and are displayed on a display of the at least one pharmacy system, whereby entry and transcription errors are reduced, wherein the multi-path clearinghouse automatically correlates a specific query initiated by one of the at least one pharmacy system, and directed to a specific prescriber, wherein the specific prescriber is a specific one of the at least one prescriber of the plurality of physician office practice management systems, with an answer from the specific prescriber, when the specific prescriber answers the specific query, and the multi-path clearinghouse correlates the answer from the specific prescriber to the specific query of the one of the at least one pharmacy system that initiated the specific query via a reply server of the multi-path clearinghouse, the reply server of the multi-path clearinghouse comprises a processor and computer memory programmed to correlate automated two-way digital communications between the specific prescriber and the one of the at least one pharmacy system that initiated the specific query via at least two paths, wherein the specific query is transmitted to the specific prescriber via both of the at least two paths, and the reply server of the multi-path clearinghouse is arranged such that the answer from the specific prescriber is routed to the one of the at least one pharmacy system that initiated the specific query regardless of which of the at least two paths that the specific prescriber uses to answer the specific query, wherein the at least two paths includes a first path and a second path, and the first path of the at least two paths sends the specific query via the physician office practice management system from which the electronic prescription was transmitted by the specific prescriber, and the second path of the at least two paths sends an alert by a system separate from the physician office practice management system from which the electronic prescription was transmitted by the specific prescriber, sending the alert to the specific prescriber alerting the specific prescriber to answer the specific query by selecting an answer or a link provided in the alert via the second path back to the reply server of the multi-path clearinghouse, and the reply server is arranged to correlate the answer of the specific prescriber with the specific query regardless of which path the specific prescriber received the specific query and which path the specific prescriber selects to reply to the specific query, automatically updating at least one of the fields of the database of the one of the at least one pharmacy system;

wherein the multi-path clearinghouse comprises automated two-way digital communications between the at least one pharmacy system and any of the plurality of physician office practice management systems having access to the multi-path clearinghouse, wherein two-way digital communications is defined as comprising delivery of the electronic prescription from the specific prescriber of any of the plurality of physician office practice management systems directed to one of the at least one pharmacy system such that the multi-path clearinghouse directs the electronic prescription to the one of the at least one pharmacy system and receipt of the specific query initiated by the one of the at least one pharmacy system about the electronic prescription back to the specific prescriber via the multi-path clearinghouse such that, when the specific prescriber provides an immediate response to the specific query of the one of the at least one pharmacy system using the any of the plurality of physician office practice management systems via the multi-path clearinghouse, the multi-path clearinghouse immediately directs the immediate response back to the at least one pharmacy system that initiated the specific query; and wherein the multi-path clearinghouse is electronically arranged between the plurality of physician office practice management systems and the at least one pharmacy system, such that the electronic prescription is transmitted to the multi-path clearinghouse from any of the plurality of physician office practice management systems and is directed to any of the at least one pharmacy system; and wherein the reply server of the multi-path clearinghouse directs the answer back to the at least one pharmacy system that originated the specific query, without speaking by telephone or any other human intervention.

2. The electronic prescription processing system of claim 1, wherein, the reply server includes a batch processor for automatically correlating any of a plurality of queries from one or more of the at least one pharmacy system in a batch process using a single electronic transmission from one of the plurality of physician office practice management systems.

3. The electronic prescription processing system of claim 1, wherein the multi-path clearinghouse includes an alternative drug selection system, when the electronic prescription is received by the multi-path clearinghouse from one of the plurality of physician office practice management systems; and the alternative drug selection system provides one or more alternatives to the plurality of physician office practice management systems for selection by the specific prescriber on a display of the one of the plurality of physician office practice management systems, the electronic prescription processing system awaiting selection of the one or more alternatives before the multi-path clearinghouse submits the electronic prescription to the at least one pharmacy system, wherein the electronic prescription processing system intercepts the electronic prescription and automatically queries the specific prescriber whether the one or more alternatives should be substituted before the multi-path clearinghouse submits the electronic prescription to the at least one pharmacy system.

4. The electronic prescription processing system of claim 1, wherein the multi-path clearinghouse includes a verification system, the verification system operably verifying the identity and authority of the specific prescriber to enter the electronic prescription by verifying an electronic signature, biometric data, a password or a combination thereof.

5. The electronic prescription processing system of claim 4, wherein the verification system of the multi-path clearinghouse verifies the identity and authority of the specific prescriber to enter the electronic prescription using the electronic signature.

6. The electronic prescription processing system of claim 1, wherein the multi-path clearinghouse correlates a single transmission from the specific prescriber operating in a batch mode to a plurality of queries from one or more of the at least one pharmacy system.

7. The electronic prescription processing system of claim 1, further comprising a biometric data reader, wherein the biometric data reader captures biometric data of the specific prescriber, and the electronic prescription processing system uses the biometric data of the specific prescriber to authenticate the electronic prescription or a change to the electronic prescription authorized by the specific prescriber.

8. The electronic prescription processing system of claim 1, further comprising an interface system coupled to at least one of the plurality of physician office practice management systems such that the interface system couples the at least one of the plurality of physician office practice management systems to the multi-path clearinghouse, wherein two-way digital communications are established between the interface system and the multi-path clearinghouse.

9. The electronic prescription processing system of claim 1, wherein the multi-path clearinghouse comprises a notification system arranged to provide a notification of an alternative pharmacy or a substitute prescription item to the plurality of physician office practice management systems, if a drug or at least one acceptable alternative drug is not available from the at least one pharmacy system originally selected or if the drug or the at least one alternative drug is available at lower cost to a patient or an insurance plan, the notification system presenting the plurality of physician office practice management systems an option for selecting the alternative pharmacy or the substitute prescription item, and waiting for a response before transmitting the electronic prescription.

10. The electronic prescription processing system of claim 1, wherein the multi-path clearinghouse includes a timer and the timer triggers when the answer is not timely.

11. The electronic prescription processing system of claim 1, wherein the automated two-way digital communications of the multi-path clearinghouse includes a unique query identifier in the specific query and the answer, and the unique query identifier is used to correlate the answer with the specific query, automatically updating the pharmacy system database with the answer to the specific query when the answer is received at the reply server.

12. The electronic prescription processing system of claim 11, wherein the automated two-way digital communications of the multi-path clearinghouse transmits the specific query with the link back to the reply server.

13. The electronic prescription processing system of claim 12, wherein the link back to the reply server provides access to the reply server for answering the specific query on the reply server, automatically updating the pharmacy system database with the answer to the specific query.

14. The electronic prescription processing system of claim 1, wherein the automated two-way digital communications of the multi-path clearinghouse transmits the specific query with the link back to the reply server.

15. The electronic prescription processing system of claim 14, wherein the link back to the reply server provides access to the reply server for answering the specific query on the reply server, automatically updating the pharmacy system database with the answer to the specific query.

* * * * *